(12) United States Patent
McElvany

(10) Patent No.: US 10,894,069 B2
(45) Date of Patent: Jan. 19, 2021

(54) TOPICAL ANTIVIRAL FORMULATIONS AND METHODS OF USING THE SAME

(71) Applicant: Christopher A. McElvany, Denver, CO (US)

(72) Inventor: Christopher A. McElvany, Denver, CO (US)

( * ) Notice: Subject to any disclaimer, the term of this patent is extended or adjusted under 35 U.S.C. 154(b) by 0 days.

(21) Appl. No.: 16/664,471

(22) Filed: Oct. 25, 2019

(65) Prior Publication Data

US 2020/0230187 A1 Jul. 23, 2020

Related U.S. Application Data

(63) Continuation of application No. 15/744,935, filed as application No. PCT/US2016/042595 on Jul. 15, 2016, now Pat. No. 10,456,435.

(60) Provisional application No. 62/192,893, filed on Jul. 15, 2015.

(51) Int. Cl.

| | |
|---|---|
| *A61K 36/00* | (2006.01) |
| *A61K 36/185* | (2006.01) |
| *A61K 9/00* | (2006.01) |
| *A61K 9/06* | (2006.01) |
| *A61K 9/107* | (2006.01) |
| *A61K 47/44* | (2017.01) |
| *A61K 31/352* | (2006.01) |
| *A61K 9/50* | (2006.01) |
| *A61K 8/02* | (2006.01) |
| *A61K 8/34* | (2006.01) |
| *A61K 8/9789* | (2017.01) |
| *A61K 8/49* | (2006.01) |
| *A61K 8/92* | (2006.01) |
| *A61Q 19/00* | (2006.01) |
| *A61K 31/05* | (2006.01) |
| *A61P 31/22* | (2006.01) |
| *A61K 47/10* | (2017.01) |
| *A61K 31/522* | (2006.01) |

(52) U.S. Cl.
CPC .......... *A61K 36/185* (2013.01); *A61K 8/0229* (2013.01); *A61K 8/347* (2013.01); *A61K 8/498* (2013.01); *A61K 8/4953* (2013.01); *A61K 8/922* (2013.01); *A61K 8/9789* (2017.08); *A61K 9/0014* (2013.01); *A61K 9/06* (2013.01); *A61K 9/107* (2013.01); *A61K 9/50* (2013.01); *A61K 31/05* (2013.01); *A61K 31/352* (2013.01); *A61K 47/10* (2013.01); *A61K 47/44* (2013.01); *A61P 31/22* (2018.01); *A61Q 19/001* (2013.01); *A61K 31/522* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 2,798,053 A | 7/1957 | Brown |
| 4,509,949 A | 4/1985 | Huang et al. |
| 4,963,555 A | 10/1990 | Jones et al. |
| 5,087,445 A | 2/1992 | Haffey et al. |
| 6,193,985 B1 | 2/2001 | Sonne |
| 8,642,645 B2 | 2/2014 | Kelly |
| 8,846,409 B2 | 9/2014 | Flock-Hart et al. |
| D909,556 | 8/2015 | Sekura et al. |
| 10,456,435 B2 | 10/2019 | McElvany |
| 2008/0075793 A1 | 3/2008 | Dunshee et al. |
| 2011/0274676 A1 | 11/2011 | Farmer et al. |
| 2012/0237466 A1 | 9/2012 | Graham |
| 2014/0302121 A1 | 10/2014 | Bevier |

FOREIGN PATENT DOCUMENTS

| | | |
|---|---|---|
| WO | WO 02/064109 | 8/2002 |
| WO | WO 2014/152385 | 9/2014 |

OTHER PUBLICATIONS

Beylier et al., "Bacteriostatic Activity of Some Australian Essential Oils," Perfumer & Flavorist, vol. 4. 1979, pp. 23-25.
Cornwell et al., "Glyceryl monocaprylate/caprate as a moderate skin penetration enhancer," International Journal of Pharmaceutics, vol. 171, No. 2, 1998, pp. 243-255.
Gupta et al., "Genitai Herpes," The Lancet, vol. 370, No. 9605, 2007, pp. 2127-2137.
International Search Report and Written Opinion for International (PCT) Application No. PCT/US16/42595, dated Oct. 4, 2016, 12 pages.
International Preliminary Report on Patentability for International (PCT) Application No. PCT/US16/42595, dated Jan. 25, 2018, 10 pages.
Notice of Allowance for U.S. Appl. No. 15/744,935, dated Jun. 25, 2019, 10 pages.

*Primary Examiner* — Michael V Meller
(74) *Attorney, Agent, or Firm* — Sheridan Ross P.C.

(57) ABSTRACT

Antiviral pharmaceutical compositions comprising one or more cannabinoid compounds in the form of lip-balms, creams and ointments. A specific embodiment provides a topical composition formulated as a lip-balm.

2 Claims, No Drawings

TOPICAL ANTIVIRAL FORMULATIONS AND METHODS OF USING THE SAME

CROSS REFERENCE TO RELATED APPLICATION

This application is a continuation of U.S. patent application Ser. No. 15/744,935, filed Jan. 15, 2018, now U.S. Pat. No. 10,456,435, which is a national stage application under 35 U.S.C. 371 of PCT Application No. PCT/US2016/042595 having an international filing date of Jul. 15, 2016, which designated the United States, which PCT application claimed the benefit of U.S. Provisional Patent Application No. 62/192,893, filed Jul. 15, 2016, both of which are incorporated herein by reference.

TECHNICAL FIELD

The disclosure provides antiviral pharmaceutical compositions comprising one or more cannabinoid compounds in the form of lip-balms, creams and ointments. A specific embodiment discloses a lip-balm composition comprising tetrahydrocannabinol.

BACKGROUND OF DISCLOSURE

Herpes simplex virus (HSV) infections are ubiquitous, with approximately 80% of the adult population infected with HSV type 1 and approximately 20% of the adult population also infected with HSV type 2. HSV type 1 is the cause of herpes labialis, also called orofacial herpes, or cold sores, and HSV encephalitis. HSV type 2 is the primary cause of initial and recurrent genital herpes, and neonatal HSV. The typical manifestation of a primary HSV-1 or HSV-2 genital infection is clusters of inflamed papules and vesicles on the outer surface of the genitals resembling cold sores. (Gupta et al., 2007, Lancet 370(9605): 2127-37). Varicella zoster virus, also known as chickenpox, Varicella virus, zoster virus, and human herpes virus type 3 (HHV-3), results in chickenpox which generally occurs in children and young people. Even when clinical symptoms of chickenpox have resolved, Varicella zoster virus remains dormant in the nervous system of the infected person (virus latency), in the trigeminal and dorsal root ganglia. In about 10-20% of cases, Varicella zoster virus reactivates later in life causing herpes zoster or shingles, an illness with very different symptoms.

Herpes viruses cycle between periods of active disease, presenting as blisters containing infectious virus particles that typically persists for a period between 2-21 days, followed by a remission period, during which the sores disappear. Many HSV infected people experience recurrence within the first year of infection. During recurrence, fewer lesions are likely to develop, lesions are less painful, and lesions heal faster than those occurring during the primary infection. Subsequent outbreaks tend to be periodic or episodic, occurring on average four to five times a year when the patient is not using antiviral therapy.

Treatment of initial HSV infection and reactivated latent HSV infection typically includes the topical application of an antiviral nucleoside compositions to lesions at the first sign of outbreak, and at recurring intervals until remission of the lesions. Current prescription topical treatments for herpes labialis include Zovirax™ cream (5% acyclovir, GlaxoSmithKline/Biovail Pharmaceuticals) which is FDA approved for the treatment of recurrent herpes labialis (cold sores) in adults and adolescents over 12 years of age. Another topical treatment is Denavir™ (1% penciclovir, Novartis), which is FDA approved for the treatment of recurrent cold sores in adults. These treatments inhibit viral replication, shortening healing time and duration of symptoms. Zovirax™ ointment (5% acyclovir, GlaxoSmithKline/Biovail Pharmaceuticals) is approved for topical administration and is indicated in the management of initial genital herpes and in limited non-life-threatening mucocutaneous Herpes simplex virus infections in immunocompromised patients. Side effects include mild pain upon application, pruritis, and rash.

Patient satisfaction with current remedies, particularly for HSV-1, herpes labialis, has been poor, as topical acyclovir therapy lacks efficacy in comparison with oral or parenteral administrations. This may be due to poor absorption, because acyclovir concentrations in the skin following topical application is about 2-3 times lower than concentrations following oral administration. Thus, this lack of efficacy of acyclovir following topical treatment may be related to the poor water-solubility and lipophilicity of the drug, resulting in its inadequate skin or mucous membrane penetration. Despite this limited solubility and efficacy, local administration of acyclovir is still considered safer than systemic administration. Viral resistance to acyclovir is common and may result from qualitative and quantitative changes in the viral TK and/or DNA polymerase; particularly in immunocompromised patients. Clearly, there is room for improvement in topical antiviral compositions for the rapid, efficacious treatment of HSV infections.

In view of the foregoing, there is a need for topical formulations that comprise a less toxic and more generally effective topical drug product that can be used daily for preventing reactivation of latent HSV infection and recurrence of herpes skin and mucus membrane lesions.

SUMMARY

Materials derived from the botanical genus *Cannabis* produce approximately 80 distinct entities classified as cannabinoids, including tetrahydrocannabinol (THC) and cannabidiol (CBD). These chemicals have been reported to have diverse pharmacological activities that include analgesic, anti-inflammatory, anti-cancer, antibiotic, and anti-oxidant activity.

The disclosure provides a topical antiviral composition comprising therapeutically effective amounts of one or more cannabinoid compounds. The cannabinoid may be selected from one or more of THC and CBD or pharmaceutically acceptable salts or esters thereof. The therapeutically effective amount of one or more cannabinoid compounds may be provided as an extract of the marijuana plant. The cannabinoid may be CBD, or pharmaceutically acceptable salts or esters thereof, that are substantially or completely free of THC. The therapeutically effective amount of CBD may be provided as an extract of the hemp plant.

The topical composition may be prepared in a form selected from a lip-balm, stick, cream or ointment. In one specific aspect, the topical composition is in a lip-balm form. In one specific aspect, the topical composition is in a lip-gloss form. In an exemplary aspect, the composition further comprises one or more polyethylene glycol(s). In an exemplary aspect, composition further comprises an astringent. In an exemplary aspect, the astringent may be tea tree oil. In an exemplary aspect, the composition further comprises vitamin E. In an exemplary aspect, the composition further comprises one or more moisturizing agents. In an exemplary aspect, the composition is free of any petroleum products. In another aspect, the composition optionally further comprises one or more sweeteners or flavorings.

The composition may comprise from about 1 wt % to about 50 wt % of cannabinoids. In one aspect, the composition comprises about 5 wt % to about 20 wt % of cannabinoids.

The disclosure also provides a method of treating a herpes viral infection of the skin or mucosa of a mammal which comprises applying to the skin or mucosa a topical composition comprising a therapeutically effective amount of a cannabinoid, or a pharmaceutically acceptable salt or ester thereof. The method of treating may include applying to the skin or mucosa a composition comprising one or more cannabinoids selected from the group consisting of 2-arachidonylglycerol; N-arachidonyl-1-(2,3-dichlorobenzoyl)-2-methyl-3-(2-[1-morpholino]ethyl)-5-methoxyindole; 2-methyl-1-propyl-3-(1-naphthoyl)indole; 1-methoxy-N,N-dimethylmethanamide; 1-methoxy-endo-4-hydroxy-9-oxabicyclo(3.3.1)nonane; dronabinol; (2-methyl-1-propyl-1H-indol-3-yl)-1-naphthalenylmethanone; 3-(1,1-dimethylbutyl)-6a,7,10,10a-tetrahydro-6,6,9-6h-dibenzo[b,d]pyran; [2,3-dihydro-5-methyl-3(4-morpholinylmethyl) pyrrolo[1,2,3-de]methane; 5-(1,1-dimethylheptyl)-2-[(1R,2R,5R)-5-hydroxy-2-(3-hydroxypropyl)cyclohexyl]phenol; 5-(4-chlorophenyl)-1-(2,4-dichlorophenyl)-4-methyl-N-1-piperidinyl-1H-pyr-azole-3-caroxamide; [6-methoxy-2-(4-methoxyphenyl)benzo[b]furan-3-yl](4-cyanophenyl)methanone; [6-iodo-2-methyl-1-[2-(4-morpholinyl)ethyl]-1H-indol-3-yl](4-methoxy phenyl)methanone; 5-(4-chloro-3-methylphenyl)-1-[(4-methylphenyl)methyl]-N-(1,3,3-trimethyl-bicyclo[2.2.1]hept-2-yl)-(1S-endo)-1H-pyrazole-3-carboxamide; 1-(2,4-dichlorophenyl)-5-(4-iodophenyl)-4-methyl-n-1-piperidinyl-1H-pyraz-ole-3-carboxamide; 1-(2, 4-dichlorophenyl)-5-(4-iodophenyl)-4-methyl-N-4-morpholinyl-1H-pyraz-ole-3-carboxamide; 3-(6-azido-2-hexynyl)-6a,7,10,10a-tetrahydro-6,6,9-trimethyl-(6aR, 10aR)-6-H-dibenzo[b,d]pyran-1-ol; 3-[(2Z)-6-azido-2-hexynyl]-6a,7,10, 10a-tetrahydro-6,6,9-trimethyl-(6aR,10-aR)-6H-dibenzo[b,d]pyran-1-ol; (−)-6,7-dichloro-1,4-dihydro-5-[3-(methoxymethyl)-5-(3-pyridinyl)-4H-1,2,-4-triazol-4-yl]-2,3-quinoxalinedione; (2R,4S)-rel-5,7-dichloro-1,2,3,4-tetrahydro-4-[[(phenylamino)carbonyl] ami-no]-2-quinolinecarboxylic acid; (2R,6S)-1,2,3,4,5,6-hexahydro-3-[(2S)-2-methoxypropyl]-6,11,11-trimethyl-2, 6-methano-3-benzazocin-9-ol; (3E)-2-amino-4-(phosphonomethyl)-3-heptenoic acid; (3R,4S)-rel-3,4-dihydro-3-[4-hydroxy-4-(phenylmethyl)-1-piperidinyl]-2H-1-1-benzopyran-4,7-diol; (3S,4aR,6S,8aR)-decahydro-6-(phosphonomethyl)-3-isoquinoline carboxylic acid; (R)-9-bromo-2,3,6,7-tetrahydro-2,3-dioxo-N-phenyl-1H,5H-pyrido[1,2,-3-de]quinoxaline-5-acetamide; (.alpha.R)-.alpha.-amino-5-chloro-1-(phosphonomethyl)-1H-benzimidazole-2-propanoic acid; [2-(8,9-dioxo-2,6-diazabicyclo[5.2.0]non-1(7)-en-2-yl)ethyl]-phosphonic acid; [5-(aminomethyl)-2-[[[(5S)-9-chloro-2,3,6,7-tetrahydro-2,3-dioxo-1H,5H-py-rido[1,2,3-de]quinoxalin-5-yl] acetyl]amino]phenoxy]-acetic acid; 1,4-dihydro-6-methyl-5-[(methylamino)methyl]-7-nitro-2,3-quinoxaline-dion-e monohydrochloride; 1-[2-(4-hydroxyphenoxy)ethyl]-4-[(4-methylphenyl)methyl]-4-piperidinol hydrochloride; 1-[4-(1H-imidazol-4-yl)-3-butynyl]-4-(phenylmethyl)-piperi-dine; 1-aminocyclopentane-carboxylic acid (ACPC); 2-[(2, 3-dihydro-1H-inden-2-yl)amino]-acetamide monohydrochloride; 2-hydroxy-5-[[(pentafluorophenyl) methyl]amino]-benzoic acid (PBAS); 2-methyl-6-(phenyl-ethynyl)-pyridine (MPEP); 3-(phosphonomethyl)-L-phenyl-alanine; 3-[(1E)-2-carboxy-2-phenylethenyl]-4,6-dichloro-1H-indole-2-carboxylic acid; 4,6-dichloro-3-[(E)-(2-oxo-1-phenyl-3-pyrrolidinylidene)methyl]-1H-indole-2-carboxylic acid; 6-chloro-2,3,4,9-tetrahydro-9-methyl-2,3-dioxo-1H-indeno[1,2-b]pyrazine-9-1-acetic acid; 11-hydroxy-9,15-dioxoprosta-8,12,13-dienoic acid; 2-[3-methyl-6-(1-methylethenyl)-2-cyclohexen-1-yl]-5-pentyl-(1R-trans)-1,-3-benzenediol (cannabidiol); 3-amyl-1-hydroxy-6,6,9-trimethyl-6H-dibenzo[b,d]pyran (cannabinol); 3-(1,1-dimethylheptyl)-6a,7,8,9,10,10a-hexahydro-1-hydroxy-6,6-dimethyl-(-6aR,9R,10aR)-6H-dibenzo[b,d] pyran-9-methanol; 7-(1,1-dimethylheptyl-1,2,3,4,4a,9b-hexahydro-2,2-dimethyl-4-methylene-1-,3-methanodibenzofuran-9-ol; 7-(1,1-dimethylheptyl)-1,2,3,4, 4a,9b-hexahydro-2,2-dimethyl-4-methylene-1-(s),3-methanodibenzofuran-9-ol; 2-[4-[(acetyloxy)methyl]-6,6-dimethylbicyclo[3.1.1]hept-3-en-2-yl]-5-(1,1-dimethylheptyl)-diacetate[1R-(1a,2a,5a)]-1,3-benzenediol; 2-[4-[(acetyloxy)methyl]-6,6-dimethylbicyclo[3.1.1]hept-3-en-2-yl]-5-(1,1-dimethylheptyl)-diacetate[1S-(1a,2a,5a)]-1, 3-benzenediol; 5-(1,1-dimethylheptyl)-2-[4-(hydroxymethyl)-6,6-dimethylbicyclo[3.1.1]hep-t-3-en-2-yl]-[1S-(1a, 2a,5a)]-1,3-benzenediol; and 5-(1,1-dimethylheptyl)-2-[4-(hydroxymethyl)-6,6-dimethylbicyclo[3.1.1]hep-t-3-en-2-yl]-[1R-(1a,2a,5a)]-1,3-benzenediol; or an isomer, or a pharmaceutically acceptable salt, or ester thereof.

In one aspect, the method of treating includes topical application of the composition in a form selected from a lip-balm, lip-gloss, stick, cream or ointment. In one specific aspect, the topical composition is in a lip-balm form. In one aspect, the method of treating includes topical application of the composition which further comprises one or more polyethylene glycols. In another aspect, the method of treating includes topical application of the composition further comprising one or more sweeteners or flavorings. In one aspect, the method is for the treatment of latent infection of Herpes simplex type 1 infection. In another aspect, the method is for treatment of latent infection of Herpes simplex type 2 infection.

The disclosure further provides a method of reducing the duration of a herpes viral infection outbreak of the skin or mucosa of a mammal which includes applying to the skin or mucosa a topical composition of this disclosure that comprises a therapeutically effective amount of a cannabinoid, or a pharmaceutically acceptable salt thereof. In one aspect this method is for treatment of Herpes simplex type 1 infection. In another aspect, the method is for treatment for Herpes simplex type 2 infection.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. Additional aspects of the present disclosure will become more readily apparent from the Description of Embodiments, particularly when taken together with the drawings.

DESCRIPTION OF EMBODIMENTS

The present disclosure is drawn to a product of treating or suppressing latent herpes virus recurrence that advantageously has few unintended or unwanted effects or drug interactions and greatly increases the healing of latent herpes virus skin lesions and substantially decreases the number of recurrent latent herpes virus skin lesion outbreaks following prophylactic treatment.

The disclosure provides topical antiviral pharmaceutical compositions comprising one or more cannabinoids and methods of using such compositions to treat or prevent latent herpes virus skin lesions. The topical antiviral compositions may be prepared in the form of a lip-balm, stick, cream, ointment, lotion, gel, or pen. Specific embodiments are lip-balm stick and lip-gloss compositions comprising at least one cannabinoid. The cannabinoid may be one or both of tetrahydrocannabinol (THC) and cannabidiol (CBD).

The present invention provides compositions that include therapeutically effective amounts of a cannabinoid, or a pharmaceutically acceptable salt or ester thereof, together with an acceptable topical carrier.

Unless indicated otherwise, the indefinite articles "a" and "an" are synonymous with "at least one" or "one or more." Unless indicated otherwise, definite articles used herein, such as "the," also include the plural of the noun. Terms used herein such as "comprising," "consisting essentially of," and "consisting of" have their ordinary and customary meaning under U.S. patent law. Unless otherwise indicated, the transitional term "comprising" is synonymous with "including," "containing," or "characterized by" and is inclusive or open-ended and does not exclude additional, unrecited elements or method stages. Unless otherwise indicated, the transitional term "consisting essentially of" limits the scope of the claim to the materials specified and/or recited in the body of the claim or method stages specified and/or recited in the body of the claim, and this transitional phrase excludes those materials or stages that materially affect the basic and novel characteristics of the claimed invention. Unless otherwise indicated, the transitional term "consisting of" limits the scope of the claim to only those materials specified and/or recited in the body of the claim or to only those method stages specified and/or recited in the body of the claim.

Unless otherwise indicated, the term "*Cannabis*" used herein refers to at least one of *Cannabis sativa* and *Cannabis indica*. Some of the materials which are produced by the *Cannabis* species have been shown to have pharmacologic activity.

Tetrahydrocannabinol, which is abbreviated herein as "THC" unless otherwise indicated, is the principal psychoactive constituent (or cannabinoid) of the cannabis plant. THC is also known as delta-9-tetrahydrocannabinol (Δ9-THC). THC was first isolated in 1964, and, in its pure form, it is a glassy solid when cold and becomes viscous and sticky if warmed. THC is an aromatic terpenoid, and it has a very low solubility in water but good solubility in most organic solvents, specifically lipids and alcohols. THC also exhibits high UV-B (280-315 nm) absorbance.

Cannabidiol (CBD) is one of at least 85 cannabinoids found in cannabis. It is a major constituent of the plant, second to THC, and represents up to 62% in its extracts. Compared with THC, cannabidiol is non-psychoactive, and is considered to have a wider scope of medical applications than THC.

The phrase "acceptable carrier" as used herein means an acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which may serve as acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and waxes, including, but not limited to, beeswax, synthetic beeswax, carnuba wax; (9) oils, such as peanut oil, coconut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) astringents such as Tea Tree Oil; (16) pyrogen-free water; (17) isotonic saline; (18) Ringer's solution; (19) ethyl alcohol; (20) phosphate buffer solutions; (21) silica gel; and (22) other non-toxic compatible substances employed in pharmaceutical or cosmetic formulations.

Compositions of the present invention can be pharmaceutically or cosmetically elegant or can have pleasant tactile properties. "Pharmaceutically elegant," and/or "cosmetically elegant," describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and refers to ranges within 10%, within 5%, within 1%, or within 0.5%.

"Optional" or "optionally" means that the subsequently described ingredient may or may not be included in disclosed compositions. "Optionally" is inclusive of embodiments in which the described ingredient is present and embodiments in which the described ingredient is not present.

The use of "wt %" and "w/w" indicates the relative weight percent of a specified ingredient when compared to the weight of the total formulation, unless otherwise specified. Also included in the family of compounds of the present invention are the pharmaceutically acceptable salts, and esters thereof. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention can be prepared from inorganic acid or from an organic acid. Examples of such inorganic acids include hydrochloric, hydrobromic, hydroiodic, nitric, carbonic, sulfuric, and phosphoric acid. Appropriate organic acids may include aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The compositions are preferably formulated for topical administration, including formulations suitable for application to skin, mucus membranes and male and female genitalia.

The term "inhibit" or "inhibiting" refers to a statistically significant and measurable reduction in activity or occurrence, preferably a reduction of at least about 10% versus control, more preferably a reduction of about 20% or more, still more preferably a reduction of about 30% or more.

A "therapeutically effective amount" is an amount of a cannabinoid compound, or compounds, or botanical extract of the invention, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art. For example, in reference to the treatment of a latent herpes viral infection using the compositions of the present invention, a therapeutically effective amount refers to that amount of cannabinoid(s) which have the effect of (1) reducing the pain, tingling, burning or itching of the outbreak, (2) reducing the duration of the outbreak, (3) reducing the recurrence of outbreaks, and/or, (4) relieving to some extent (or, preferably, eliminating) one or more other symptoms associated with the outbreak such as, for example, ulceration, crusting, weeping and scabbing.

The term "subject" or "patient" refers to an animal, for example a mammal, who is the object of treatment. Preferably, the patient is a human. The subject, or patient, may be either male or female.

There is no treatment that kills or causes complete elimination of the herpes virus from an infected mammal. The herpes virus therefore remains in a latent form in the skin. Because there is no known treatment to kill the herpes virus, or effectively prevent recurrent outbreaks of the lesions, recurrent herpes virus lesions are common. HSV-1 and HSV-2 are highly homologous, sharing approximately 50% of their DNA and having over 80% of common antigens. Both types infect the body's mucosal surfaces, usually the mouth or genitals, and then establish latency in the nervous system. For both types, at least two-thirds of infected people have no symptoms, or symptoms too mild to notice. However, both types can recur and spread even when no symptoms are present. By the time they are teenagers or young adults, about 50% of Americans have HSV-1 antibodies in their blood. By the time they are over age 50, some 80-90% of Americans has HSV-1 antibodies. By comparison, almost all HSV-2 is encountered after childhood, when people become sexually active.

HSVs tend to infect cells of ectodermal origin. After direct exposure to infectious material (i.e., saliva, genital secretions), initial viral replication occurs at the entry site in the skin or mucous membrane. After the initial nonspecific inflammatory response to primary infection, specific antibody response occurs in a few days, followed by a cellular immune response in the second or third week. In persons with cellular immune defects, primary HSV infection can result in life-threatening disseminated disease. In rare cases, the initial replication may lead to disease and life-threatening infection (e.g., encephalitis). After retrograde axonal flow from neurons at the viral point of entry and local replication, the viral genome becomes latent.

HSV latency is defined as the ability to remain in a non-replicating form in the dorsal root ganglia of the CNS. No viral particles are produced during latency. A stimulus (e.g., physical or emotional stress, fever, ultraviolet light) reactivates the virus in the form of skin vesicles or mucosal ulcers, with symptoms less severe than those of the primary infection. Latent HSV can be reactivated from the trigeminal, sacral, and vagal ganglia. Herpes labialis is the most frequent clinical sign of reactivation of HSV infection.

Herpes labialis, also called orofacial herpes, or cold sores, is most often caused by Herpes simplex Virus Type 1 (HSV-1). Reactivation of HSV, predominantly HSV-1, is rarely associated with systemic signs and symptoms; rather a prodrome of localized pain, tingling (parasthesia), burning, or itching frequently precede recurrent orolabial lesions.

Herpes labialis outbreak proceeds through several stages. Outbreaks can be triggered by any one of several factors including stress, sunlight, fatigue, fever, illness, poor diet, food allergy, and hormonal changes. The prodrome stage may last from a few hours to a few days and is generally accompanied by a tingling or burning sensation around the lips or nose. The blister stage occurs within a day or two of the prodrome stage, there is the first visible sign of clusters of small blisters. The blister stage is followed by the weeping/ulcer stage. This stage is characterized by rupture of the blisters leaving a shallow reddish ulceration. This is the most painful and contagious stage. Viral shedding occurs generally during the first 4-5 days of outbreak commencing during the prodrome stage. The weeping ulcer stage is followed by the crusting stage. A scab with a brown crust forms. If the scab cracks, the sufferer will experience itching, burning and bleeding. The healing stage follows the crusting stage. If a scab has formed, it will flake off during the healing stage.

In recurrent herpes infection/outbreak, the lesions tend to recur at the same site. Pain is most severe at the onset of infection and diminishes after 4-5 days. Patients with primary immunodeficiencies, AIDS, malignancy, malnutrition, or burns and transplant recipients (e.g., bone marrow, organs) receiving immunosuppressive therapy can have unusually severe HSV infections. Beginning antiviral treatment when prodrome symptoms are experienced reduces the appearance and duration of lesions in some individuals.

Genital herpes (herpes genitalis) is a sexually transmitted disease (STD) caused by the Herpes simplex viruses type 1 (HSV-1) or type 2 (HSV-2). Most genital herpes is caused by HSV-2. Most individuals have no or only minimal signs or symptoms from HSV-1 or HSV-2 infection. When signs do occur, they typically appear as one or more blisters on or around the genitals or rectum. The blisters break, leaving tender ulcers (sores) that may take two to four weeks to heal the first time they occur. Typically, another outbreak can appear weeks or months after the first, but it almost always is less severe and shorter than the first outbreak. Although the infection can stay in the body indefinitely, the number of outbreaks tends to decrease over a period of years. As in herpes labialis, beginning antiviral treatment when prodrome symptoms are experienced can reduce the appearance and duration of lesions.

Herpes zoster or shingles is a herpes viral disease. Years or decades after the initial chickenpox infection, the virus may break out of nerve cell bodies and travel down nerve axons to cause viral infection of the skin in the region of the nerve. The virus may spread from one or more ganglia along nerves of an affected segment and infect the corresponding dermatome (an area of skin supplied by one spinal nerve) causing a painful rash. The earliest symptoms of herpes zoster, including headache, fever, and malaise, are nonspecific. These symptoms are commonly followed by sensations of burning pain, itching, hyperesthesia (oversensitivity), or paresthesia (tingling, pricking, or numbness). The pain may be mild to extreme in the affected dermatome, with sensations that are often described as stinging, tingling, aching, numbing or throbbing, and can be interspersed with quick stabs of agonizing pain. In most cases, after one to two days, the initial phase is followed by the appearance of the characteristic skin rash. The pain and rash most commonly occurs on the torso, resulting in a stripe or belt-like pattern that is limited to one side of the body, but can appear on the face, eyes or other parts of the body. Later, the rash becomes vesicular, forming small blisters filled with a serous exudate, as the fever and general malaise continue. The painful vesicles eventually become cloudy or darkened as they fill with blood, crust over within seven to ten days, and usually the crusts fall off and the skin heals; but sometimes, after severe blistering, scarring and discolored skin remain. Although the rash usually heals within two to four weeks, some sufferers experience residual nerve pain for months or years, a condition called postherpetic neuralgia.

As used herein, reference to Herpes simplex virus infection refers to the infection caused by Herpes simplex virus-1, Herpes simplex virus-2, or both, at any area of the body. The viral disease/infection includes, but is not limited to, orofacial herpes including herpetic gingivostomatitis and herpes labialis (colloquially called cold sores or fever blisters), herpes genitalis (commonly known simply as herpes), herpetic whitlow, herpes gladiatorum, and herpetic sycosis. The Varicella zoster virus infection herein refers to the infection caused by human herpes virus-3, which includes herpes zoster (more commonly known as shingles), and chickenpox.

This disclosure provides topical antiviral compositions which reduce both the severity of symptoms and the duration of initial and recurrent HSV infection outbreaks. The topical antiviral compositions comprise one or more cannabinoids and are useful for the treatment of HSV type 1 and HSV type 2 infections. In one aspect, the disclosure provides a method for reducing reactivation of a latent infection of herpes viruses in a human comprising topically administering a composition comprising a therapeutically effective amount of a cannabinoid.

The topical antiviral compositions may contain a total of about 0.1 to about 50 wt % of one or more cannabinoids. In exemplary aspects, the topical antiviral composition comprises from about 3 wt % to about 20 wt % of cannabinoids. In exemplary aspects, the topical cannabinoid is present from about 0.5 wt % to about 10 wt % of cannabinoids. The topical cannabinoid may also be present from about 1% to about 5 wt % of the total weight of the formulation.

Cannabinoids may be obtained by separating resins from leaves of cannabis plants by solvent extraction, in which procedure cannabis is boiled in a solvent to form a viscous liquid, which is strained and the solvent is evaporated to yield an oil. Extracts derived from cannabis plants include primary extracts prepared by such processes as, for example, maceration, percolation, and solvent extraction. Solvent extraction may be carried out using essentially any solvent that dissolves cannabinoids/cannabinoid acids, such as for example $C_1$ to $C_5$ alcohols (e.g. ethanol, methanol), $C_3$-$C_{12}$ alkanes (e.g. hexane, butane or propane), Norflurane (HFA134a), HFA227, and carbon dioxide. When solvents such as these are used, the resultant extract typically contains non-specific lipid-soluble material. This can be removed by a variety of processes including "winterization", which includes chilling to $-20°$ C., followed by filtration to remove waxy ballast, extraction with liquid carbon dioxide and by distillation. General protocols for the preparation of extracts of cannabis plant material are described in International (PCT) publication No. WO 02/064109, which is incorporated herein by reference. Extraction processes capable of preparing substantially pure cannabinoid forms, or products enriched in essentially any cannabinoids or cannabinoid acids which occur naturally in plant material (including free cannabinoid forms of naturally occurring cannabinoid acids) are described in U.S. Pat. No. 8,846,409, which is incorporated herein by reference.

Carbon dioxide provides a safer way to extract cannabinoid resins from cannabis plant material. Sub Critical (Liquid) or Supercritical $CO_2$ is forced through the plant matter, which separates the cannabinoid resins and terpenes from the plant matter resulting in a transparent, amber oil. The extracts of cannabis plants are preferably obtained by supercritical fluid extraction (SFE) followed by a secondary extraction, e.g. an ethanolic precipitation, to remove a substantial proportion of non-cannabinoid materials, e.g. waxes, wax esters and glycerides, unsaturated fatty acid residues, terpenes, carotenes, and flavenoids and other ballast. Most preferably, the Botanical Drug Substance, free of ballasts, is further filtered with activated carbon to remove unwanted pigments and chlorophylls.

If it is intended to prepare free cannabinoids from the cannabis plant material, then the material is preferably heated to a defined temperature for a defined period of time in order to decarboxylate cannabinoid acids to free cannabinoids prior to extraction of the botanical drug substance.

The topical antiviral compositions may include one or more waxes. The term "wax" means a lipophilic compound that is solid at room temperature with a reversible solid/liquid change of state, having a melting point of greater than or equal to 30° C., which may be up to 200° C. The waxes may be chosen from waxes of animal, plant, mineral or synthetic origin, and mixtures thereof. Hydrocarbon-based waxes, include, for example, beeswax, lanolin wax and Chinese insect waxes; rice bran wax, carnauba wax, candelilla wax, ouricury wax, alfalfa wax, berry wax, shellac wax, Japan wax and sumach wax; montan wax, orange wax, lemon wax, microcrystalline waxes, paraffins and ozokerite; polyethylene waxes, waxy copolymers, and esters thereof. Suitable waxes may also be obtained by catalytic hydrogenation of animal or plant oils, including, for example, hydrogenated sunflower oil, hydrogenated castor oil, hydrogenated coconut oil, and hydrogenated lanolin oil. The inventive composition may contain at least one of beeswax, carnauba wax, candelilla wax, and lanolin wax. Petroleum derived waxes such as ozokerite, paraffin, and microcrystalline petroleum-based waxes may be included in the compositions of the invention, and these ingredients are common because they provide a robust stick structure and are relatively inexpensive materials. In exemplary embodiments, no petroleum derived waxes are included in the composition.

The wax may be present in the compositions of the present invention in an amount ranging from about 50% to about 95% by weight, more preferably from about 50% to about 80% by weight, most preferably from about 60% to about 75% by weight, relative to the total weight of the composition.

The topical antiviral compositions can optionally include one or more sweeteners, and/or flavors, and/or coloring agents. These optional ingredients may be added to increase patient acceptability and compliance with the recommended dosing schedule.

The sweetener may be selected from a synthetic or natural sweetener, for example, aspartame, a cyclamate, saccharin, acesulfame salts, neo-hesperidin dihydrochalcone, sucralose, alitame, astevia, stevioside, talin, glycerrhizin, thaumatin, xylitol, and mixtures thereof. The sweetener is optionally present from about 0.1% to about 5 wt % of the weight of the topical antiviral compositions.

The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. The flavor is optionally present from about 0.1% to about 5% by weight of the topical antiviral composition.

Colorants and/or opacifiers may be added to the topical compositions in order to blend with the skin tone of the patient, so long as the colorant or opacifier does not interfere with the antiviral efficacy of the formulation. Colorants include such compounds as, by way of example and without limitation, titanium dioxide, talc, FD&C Red No. 3, FD&C Red No. 20, FD&C Yellow No. 6, FD&C Blue No. 2, FD&C Green No. 5, FD&C Orange No. 5, FD&C Red No. 8, caramel, ferric oxide, other FD&C dyes, lakes, and natural coloring agents such as grape skin extract, beet red powder, beta-carotene, annato, carmine, turmeric, paprika, and other materials known in the art. The amount of coloring agent used will vary as desired.

Coloring agents may include pigments that may be used in the compositions of this disclosure to create a wide variety of visual appearances of the compositions. In certain instances, diamond pigments are used, which can create highly transparent formulations having a better luster appearance. Such pigments can also be used to create brighter colors, cleaner colors, depth, and/or sparkle to the formulations. In an exemplary aspect, the lip products, particularly lip gloss formulations of the present disclosure, include such pigments. Benefits of using diamond pigments include: (1) high levels of chromaticity, color purity, brightness, transparency and reflectivity; (2) creation of brilliant, star-like glitter effect based on their smooth surfaces and large particle size; (3) production of a true multicolor effect when two or more are blended; and/or (4) addition of visual depth and dimensionality because their novel substrate has a high level of transparency. Non-limiting examples of pigments that can be used in the context of the present invention include the RONASTAR®, REFLECKS®, COVAPEARL®, and CLOISONNE® line of pigments, which are commercially available from EMD Chemicals, Inc./Rona, N.J. USA (e.g., RONASTAR® NOBLE SPARKS), BASF, New Jersey USA (e.g., REFLECKS® DIMENSIONS SPARKLING RED, CLOISONNE® SATIN BRONGE, CLOISONNE® ROUGHE FLAMBE), and Sensient Cosmetic Technologies, New Jersey USA (e.g., COVAPEARL BRIGHT 933 AS).

The topical formulations may include a moisturizing or protective agent. The moisturizing agent is preferably at least one member selected from the group consisting of chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol. Other examples include acetylated lanolin, acetylated lanolin alcohol, alanine, algae extract, aloe barbadensis, aloe-barbadensis extract, aloe barbadensis gel, althea officinalis extract, apricot (*Prunus armeniaca*) kernel oil, arginine, arginine aspartate, arnica montana extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, Calendula officinalis extract, Calendula officinalis oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang (*Cananga odorata*) oil.

The amount of the moisturizing agent in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

The topical formulations may also include a sunscreen (UV-absorbing compound). The UV-absorbing compound is preferably at least one member selected from the group consisting of UV absorption agents that can be used in combination with the compositions of the present invention including chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropyl benzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). The amount of the UV-absorbing compound in the topical formulation is not limited, so long as it is a therapeutically effective amount. A preferred amount is from 0.01 to 5 wt %, relative to the total amount of the topical formulation, more preferably from 0.1 to 1 wt %, relative to the total amount of the topical formulation.

The pH of all of the compositions of this disclosure should be a pH which is safe for application to the skin and/or mucus membranes, and will provide optimal effect for the penetration of the cannabinoid(s)/cannabinoid extracts in the topical formulations. Such pH's are from about pH 3.5 to about pH 8. For topical application to skin, such as the area around the mouth, lips, eyes, the pH of the topical formulation is preferably between about pH 4 to about pH 6.5, even more preferably between about pH 5 to about pH 6. For topical application to mucus membranes, including genitalia, the pH of the topical formulation is preferably between about pH 6 to about pH 8, even more preferably between about pH 6.5 to about pH 7.5.

The topical formulations should be stable. The composition should also enable incorporation of sufficient amounts of the active ingredients to give the proper penetration characteristics. In addition to conventional excipient ingredients in lip-balms, sticks, creams, lotions, gels or ointments, compositions astringents can be advantageous. Various absorbent ointment bases, emulsion ointment bases and water soluble ointment bases and components are known in the art and may be utilized in the compositions of the present disclosure, for example, as described in Remington's Pharmaceutical Sciences, Eighteenth Ed. 1990, Mack Publishing Co., Easton Pa., pp. 1311-1314. Ointment carrier bases may include, but are not limited to, waxes, petrolatum, esters of fatty alcohols, and saturated fatty acids, oleic acid, olive oil, paraffin, starch glycerin, lanolin, cetyl alcohol, glyceryl monostearate, methylparaben, propylparaben, glycol ethers, polyethylene glycols, polyoxyl 40 stearate, and polysorbates. The composition may further comprise optional additional ingredients selected from one or more of a penetration enhancer, oil, waxy compound, surfactant, stabilizer, gelling agent, moisturizer, water, or a preservative.

Optional penetration enhancers serve to improve the absorption across the skin of the cannabinoid. Penetration enhancers include vitamin E, and vitamin E derivatives as described in U.S. Pat. No. 6,193,985, which is incorporated herein by reference; and glyceryl monocaprylate/caprate (Cornwell et al. 1998, Int. J. Pharmaceutics, 171(2): 243-255). Other penetration enhancers are described in Smith and Maibach (eds.), Percutaneous Penetration Enhancers, CRC Press, Inc., Boca Raton, Fla. (1995), which surveys the use and testing of various skin penetration enhancers.

Optional thickening agents, including thickener or gelling agents, can be added to the topical formulations of this disclosure. Thickening agents may include substances that can increase the viscosity of a composition without substantially modifying the efficacy of the cannabinoid(s) within the composition. Thickeners can also increase the stability of the compositions of the present disclosure. Suitable thickeners include hydrogenated polyisobutene or trihydroxystearin, or a mixture of both. Additional thickening agents that may be used in the topical formulations of this disclosure include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., CARBOPOL™ 900 series).

The oils, waxy compounds, gelling agents, and surfactants selected for the formulation and stabilization of these compositions are those traditionally employed in the dermatological arts. The optional oils and/or waxy compounds can constitute from 0.5% to 99.9% of the total weight of the composition. The amount of oil and/or wax depends on the actual form or physical state of the composition. Exemplary of such oils are vegetable oils (sweet almond, macadamia, coconut oil); synthetic oils such as perhydrosqualene, fatty alcohols, acids or esters (octyl palmitate, isopropyl lanolate, triglycerides including those of capric/caprylic acids), oxyethylenated or oxypropylenated fatty esters and ethers. Exemplary waxy compounds include jojoba oil, paraffin, carnauba wax and beeswax.

Exemplary surfactants (emulsifying and coemulsifying) include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (K or Na alkyl phosphate).

A preferred stabilizer includes glycol stearate or PEG-150 distearate. The stabilizer, when used, is typically present in an amount from about 0.1 to 5 weight percent of the composition.

Exemplary gelling agents include modified clays (bentones), metal salts of fatty acids (aluminum stearate), ethylene/acrylate copolymers, silicas, polyethylenes, calcium silicates or, alternatively, ethyl cellulose.

Preservatives may include tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 wt %, preferably about 0.05 to 4 wt %, and more preferably from about 0.1 to 2 wt %.

Any water used is preferably deionized water.

In one aspect, the topical compositions of this disclosure may be formulated as a semi-solid composition comprising a gel base comprising a hydrogenated polymer and a copolymer, a wax, and optionally a pigment, wherein the composition is substantially or completely anhydrous. A semi-solid composition is a composition that has a viscosity and rigidity intermediate between that of a solid and a liquid. Such formulations commonly recognized as a lip balm or lip gloss.

In one embodiment, this disclosure provides a composition including one or more cannabinoids in a lip-balm stick carrier formulation. Lip balms are in a semi-solid or solid form and are typically used to relieve chapped or dry lips by providing an occlusive layer on the lip surface to seal moisture in lips and protect the lips from external exposure. By comparison, lip glosses can take a liquid to semi-solid form and also provide the user with a cosmetic function by coloring or changing the appearance of the lips. In one aspect, the lip balm stick carrier formulation is comprised of one or more polyethylene glycols (PEGs). In a specific aspect, the lip-balm stick carrier formulation is comprised of a PEG, silica gel, a flavoring and a sweetener. The final mixture described above is poured, while still warm and fluid, into appropriate tubes and allowed to cool until solid. The resulting lip balm of the present disclosure is in the form of a stick. However, the lip balm of the present disclosure can also be marketed in a small wide mouth jar.

Lip glosses are typically applied to the lips in a liquid to soft solid form. The color of lip glosses can range from clear, translucent, to various shades of opacity, and can also have a frosted, glittered, glassy, or a metallic finish. Lip glosses are typically contained in small cylindrical containers and are applied with a rounded or sloped applicator wand (e.g., "doefoot" applicator) or a built-in lip brush or can be contained and squeezed from tubes and applied or spread with a fingertip. By comparison, a lipstick is in solid form and is opaque. This provides the lips with a more intense color shade when compared with a lip gloss. Also, lipsticks are housed in a lipstick case or tube. The solid nature of the lipstick allows the user to "push-up" or "push-down" the lipstick from the case or tube to expose the desired amount of surface area of the lipstick that is to be applied to the lips. The lip gloss formulations of this disclosure can be prepared in an elongated container that includes a wand or an applicator tip, wherein the tip is at least partially convex.

The disclosure also provides a composition including one or more cannabinoids in an aqueous cream carrier formulation. Preparation of aqueous creams is described, for example, in U.S. Pat. No. 4,963,555, which is incorporated herein by reference.

The disclosure also provides a composition including one or more cannabinoids in an ointment carrier formulation. In an exemplary aspect the ointment carrier formulation comprises polyethylene glycol.

This disclosure also provides a method of treating an HSV infection outbreak by topically administering a composition comprising one or more cannabinoids. A composition of the present disclosure can be administered topically to the affected area in a single daily dose or in multiple doses per day. In one aspect, the composition is administered four times a day. In another aspect, the composition is administered every three hours during waking hours. In another aspect, the composition is topically administered every two hours during waking hours. The treatment regimen may require administration from a single dose up to multiple daily doses for an extended period of time, for example, for several days or from one to two weeks. In one specific aspect, the treatment regimen includes topical application of the composition every 2 hours during waking hours for 5 days. The amount of cannabinoid administered per dose or the total amount administered will depend on such factors as the nature and severity of the infection, the age and general health of the patient.

For the amelioration of HSV-1 infections and/or the prevention of the recurrence of herpes lesions, application of an effective amount of a composition according to the invention to an infected area, e.g., skin surfaces such as the area around the mouth, lips, mucous membranes, and/or eyes, of a subject suffering from a herpes infection will generally range from about one to five applications per day, depending upon the area to be treated, and the severity of the symptoms.

For the control of genital herpes, i.e., HSV-2 infections, the compositions of this invention are administered intravaginally, preferably in admixture with a pharmaceutical carrier. The carrier is, of course, chosen with regard to the intended route and method of administration. In the present disclosure, administration is accomplished topically, i.e., to a, definite place or locus, in this instance, for example, the vagina, in the form of a cream, ointment, foam, jelly, medium chain triglyceride (fractionated coconut oil), or other suitable composition which lends itself to a topical vaginal dosage form. Creams and ointments are preferred forms.

In one aspect, a combination of one or more cannabinoids and Tea Tree Oil has unexpectedly been found to be more effective than either ingredient alone at inhibiting HSV infection of endothelial cells in vitro (in vitro assays for anti-HSV-1 and anti-HSV-2 mRNA activity are known to those of skill in the art.). The major constituents of Tea Tree Oil are 1-terpinen-4-ol and terpinene with minor amounts of 1,8-cineole and p-cymene, and its properties, together with those of other Australian essential oils, are described in Beylier, Perfumer & Flavorist, 4:23 (April/May 1979), which is hereby incorporated by reference. Tea Tree Oil may be substituted by other essential oils that possess antibacterial qualities. In preparing the formulations, the cannabinoid may be mixed with up to 2% (typically about 1% by weight) of oil of *Melaleuca alternifolia* (Tea Tree Oil) before being introduced into the other components of the topical formulations of this disclosure.

This disclosure also provides a method of treating an HSV infection outbreak by application of the composition of the present disclosure to a patient in need thereof. In one aspect, the disclosure provides a method of decreasing the duration of an outbreak of herpes labialis by application of the composition of the present disclosure to a patient in need thereof. In another aspect, application of the composition of the present disclosure reduces the recurrence of outbreaks of herpes labialis in a patient in need thereof. The compositions of the present disclosure also reduce the severity of outbreaks of herpes labialis in clinical patients. The compositions of the present disclosure also reduce the pain associated with outbreaks of herpes labialis in clinical patients.

Generally, in these methods, if treatment is started early at prodrome, no visual outbreak will occur. A reduction in duration and severity of symptoms is expected if treatment starts at blister or early crust. While the outbreak may persist if treatment starts after prodrome and upon verification, an improvement in symptoms occurs, including relief of stinging and/or reduction in visual severity.

Each publication or patent cited herein is incorporated herein by reference in its entirety.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

Composition A of a delta9-THC rich salve is prepared as follows: mix 0.25 g of BDS with high a delta9-THC concentration (around 50% Δ9-THC by weight) sufficiently with 0.25 ml of *Melaleuca alternifoilia* (Tea Tree) Leaf Oil to form a cannabinoid rich lotion. The cannabinoid concentration in the formed lotion is approximately 25% (w/w).

Composition B of a cannabinoid rich lotion is prepared as follows: mix 0.25 g of BDS containing a high delta9-THC concentration (around 50% delta9-THC by weight) with 100% pure petroleum jelly to form a cannabinoid rich salve. The delta9-THC concentration in the formed salve is about 25% (w/w).

Other suitable compositions that can be made in accordance with Example 1 include delta9-THC in the following concentrations: 5%, 10%, 20%, 40%, 80% (w/w) with 100% pure petroleum jelly as a medium. Other compatible, commercially available lotions or balms can also be used as a medium or carrier.

Example 2

The following emulsion was prepared using methods well known in the art.

A BDS containing about 70% delta9-THC and approximately 5% CBD was emulsified in an over-the-counter 3% propolis ointment (HERSTAT™ or COLDSORE-FX™) commonly marketed for cold sores. The emulsion prepared is in the form of a cream.

Operating with informed consent, individuals treated with the topical composition and the methods of the present invention for treating herpes virus infection, more particularly Herpes simplex and herpes zoster or shingles, as described in Examples 3 to 8.

Example 3

A now 39-year old male with a multi-year history of Herpes simplex of the lips, perioral areas, and occasionally, intraoral areas. Prior therapy included Valtrex™ and Zovirax™ (acyclovir, orally) with slight benefit and topically without benefit. The patient was given Composition A of the cannabinoid rich preparation as described in Example 1 to use topically twice a day at the first sign or prodrome that an eruption was imminent. This resulted in the prompt aborting of a full blown blistering lesion, and also a decrease in the healing time for lesions that had vesicated. Over more than 10 years of consistent early applications of the topical formulation, the patient has reported that the incidence of recurrent lesions has diminished dramatically. Patient A has been a test subject to various formulations including EXAMPLES 1-3, 7 and other formulations containing cannabinoids and has had promising results with each iteration of the topical cannabinoid rich formulations.

Example 4

A 31-year old female presented with a history of recurrent episodes of herpes labialis. Prior therapies had been unsatisfactory from the standpoint of response and cost. A sample of Composition A of the cannabinoid rich formulation of Example 1 was provided to the patient to be applied topically to the affected area of the lips twice a day upon first sign of an eruption or of an impending eruption. The patient found that the herpes labialis responded well to the topical treatment and when applied prior to vesication, would altogether cease progression of the outbreak and prevent visual evidence thereof without the high cost and identified health risks of Zovirax™ (acyclovir) or Famvir™ (famciclovir). or VALTREX™ (valacyclovir).

Example 5

A 53 year-old female with a multiyear history of herpes labials affecting multiple areas of lips and face. The patient had been on numerous different therapies including high doses of VALTREX™ (valacyclovir), all without total satisfaction. A sample of Composition A lotion of Example 1 was provided to the patient to be applied topically to the affected area twice a day. After more than three years of use, the patient has reported that the topical treatment with the cannabinoid rich lotion has had better result than the other treatment methods, but without the side effects and high cost of VALTREX™ (valacyclovir).

Numerous other patients have been treated using Composition A or B of the cannabinoid rich lotion and the method of the present invention. All have demonstrated a good to excellent response to the lotion for control of their Herpes simplex.

Example 6

A 37 year-old male presented with a decade or longer history of herpes genitalias recurring on the epithelium of the penis, more specifically the shaft. The patient had severe pain with burning and tingling that had not responded to high dose of VALTREX™ (valacyclovir). The patient was then treated with Composition B of the cannabinoid rich topical of Example 1 one to two times a day. The applied topical provided prompt relief of the pain and tingling while reducing the overall anxiety associated with a genital herpes outbreak along with diminished duration of symptoms.

Example 7

A cannabidiol (CBD) rich BDS with a Δ9-THC content of less than 0.03% and composed primarily of CBD in a white crystalline powder form and tested at approximately 92% CBD by weight and derived from Industrial Hemp.

In the above described informal trials, no adverse side effects or contra-indications were observed among the patients. The patients had no complaints of skin irritation, sensitivity or discomfort originating from the treatment.

The foregoing examples of the present disclosure have been presented for purposes of illustration and description. Furthermore, these examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. An emulsion consisting essentially of cannabis, polyoxamer, at least one compound selected from the group consisting of lecithin, stearic acid, palmitic acid, palm oil, hydrogenated palm kernel oil, and avocado oil, and at least one component selected from the group consisting of propylene glycol and polyethylene glycol.

2. The emulsion of claim 1, wherein the cannabis consists essentially of tetrahydrocannabinol or cannabidiol.

* * * * *